United States Patent
Lee et al.

(10) Patent No.: US 12,417,478 B2
(45) Date of Patent: Sep. 16, 2025

(54) SYSTEM FOR GENERATING PRODUCT RECOMMENDATIONS USING BIOMETRIC DATA

(71) Applicant: L'Oreal, Paris (FR)

(72) Inventors: Jennifer Lee, Clark, NJ (US); Fred Orsita, Clark, NJ (US); Shelby Stewart, Clark, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 17/364,395

(22) Filed: Jun. 30, 2021

(65) Prior Publication Data

US 2021/0406983 A1 Dec. 30, 2021

Related U.S. Application Data

(60) Provisional application No. 63/046,410, filed on Jun. 30, 2020.

(51) Int. Cl.
*G06Q 30/0601* (2023.01)
*A61B 5/0533* (2021.01)
(Continued)

(52) U.S. Cl.
CPC ....... *G06Q 30/0631* (2013.01); *A61B 5/0533* (2013.01); *G06F 3/014* (2013.01);
(Continued)

(58) Field of Classification Search
CPC .......................... G06Q 30/0631; A61B 5/0533
See application file for complete search history.

(56) References Cited

U.S. PATENT DOCUMENTS

| 8,533,042 B2 | 9/2013 | Pradeep et al. |
| 11,197,623 B2 | 12/2021 | Ouwerkerk et al. |

(Continued)

FOREIGN PATENT DOCUMENTS

| JP | 1995021145 A | 1/1995 |
| JP | 2006293535 A | 10/2006 |

(Continued)

OTHER PUBLICATIONS

A Multisensor Data Fusion Approach for Predicting Consumer Acceptance of Food Products. Alvarez-Pato, Victor M; Sanchez, Claudia N; Dominguez-Soberanes, Julieta; Mendoza-Perez, David E; Velazquez, Ramiro. Foods9.6: NA. MDPI AG. (Jun. 2020) (Year: 2020).*

(Continued)

*Primary Examiner* — Michael Misiaszek
(74) *Attorney, Agent, or Firm* — CHRISTENSEN O'CONNOR JOHNSON KINDNESS PLLC

(57) ABSTRACT

Systems and methods for facilitating product preferences and/or product recommendations are disclosed. Biometric data of the subject are taken into account by the systems and methods in order to determine product preferences and/or product recommendations. Other factors of the subject, although optional, may be also taken into account while determining product preferences and/or product recommendations for a subject. These product preferences or recommendations can be presented to the subject, either automatically via a display device or with assistance from a product consultant. To obtain the biometric data, the subject will be exposed to a number of stimuli, such as fragrance/scent stimuli. Biometric data will then be collected from the subject based on her response to this fragrance/scent stimuli. In some examples, the collected biometric data relates to a (Continued)

subject's Electrodermal Resistance (EDR) or Electrodermal Activity (EDA).

15 Claims, 8 Drawing Sheets

(51) Int. Cl.
    *G06F 3/01*     (2006.01)
    *G06Q 30/0203*     (2023.01)
    *G06V 40/16*     (2022.01)
    *G06V 40/20*     (2022.01)

(52) U.S. Cl.
    CPC ..... *G06Q 30/0203* (2013.01); *G06Q 30/0643* (2013.01); *G06V 40/176* (2022.01); *G06V 40/20* (2022.01)

(56) References Cited

U.S. PATENT DOCUMENTS

| | | | |
|---|---|---|---|
| 2001/0049642 A1* | 12/2001 | Harris | G06Q 30/02 705/26.7 |
| 2004/0107053 A1* | 6/2004 | Pelletier | G06F 16/9535 702/19 |
| 2006/0230108 A1 | 10/2006 | Tatsuta et al. | |
| 2008/0065468 A1* | 3/2008 | Berg | G06Q 30/02 705/7.32 |
| 2009/0222305 A1 | 9/2009 | Berg, Jr. | |
| 2013/0262182 A1 | 10/2013 | Kodra et al. | |
| 2017/0083927 A1* | 3/2017 | Niedziela | G06T 19/20 |
| 2017/0140252 A1* | 5/2017 | Stucki | G09G 5/06 |
| 2018/0089739 A1 | 3/2018 | Cecchi et al. | |
| 2019/0370878 A1* | 12/2019 | Tran | G06Q 30/0203 |
| 2020/0218415 A1* | 7/2020 | Jang | G06N 3/08 |
| 2021/0187148 A1* | 6/2021 | Sivagaminathan | G06Q 30/0631 |
| 2021/0256542 A1* | 8/2021 | Mcdaniel | G06V 40/174 |
| 2022/0138948 A1* | 5/2022 | Gaur | G16H 70/00 382/128 |

FOREIGN PATENT DOCUMENTS

| | | |
|---|---|---|
| JP | 2011513851 A1 | 4/2011 |
| JP | 2012053320 A | 3/2012 |
| JP | 2016100520 A | 5/2016 |
| JP | 2019515726 A | 6/2019 |
| KR | 10-2010-0038107 A | 4/2010 |

OTHER PUBLICATIONS

Search Report and Written Opinion mailed Apr. 29, 2021, issued in corresponding French Application No. 2009489, filed Sep. 18, 2020, 6 pages.
International Search Report and Written Opinion of the International Searching Authority mailed Nov. 15, 2021, issued in corresponding International Application No. PCT/US2021/039980, filed Jun. 30, 2021, 10 pages.
Office Action mailed Jan. 29, 2024, issued in corresponding Japanese Application No. 2022-580976, 12 pages.
European Office Action mailed on Feb. 19, 2025, issued in European Application No. 21737952.8, filed on Jun. 30, 2021; 6 pages.
Korean Office Action mailed on Jan. 18, 2025, issued in Korean Application No. 10-2023-700490, filed on Jun. 30, 2021; 18 pages.

* cited by examiner

SYSTEM FOR GENERATING PRODUCT RECOMMENDATIONS USING BIOMETRIC DATA

CROSS-REFERENCES TO RELATED APPLICATIONS

This application claims the benefit of U.S. Provisional Application No. 63/046,410, filed Jun. 30, 2020, the disclosures of which are incorporated herein in their entirety.

FIELD OF THE DISCLOSURE

Embodiments of the present disclosures relate generally to the use of biometric data as an aid in product recommendations and/or selection. In some embodiments, the biometric data is utilized to determine product preferences of a user. In some of these embodiments, the product preferences are used to aid in product recommendations and/or selection.

SUMMARY OF THE DISCLOSURE

Systems and methods for facilitating product preferences and/or product recommendations are disclosed herein. In embodiments described below, biometric data of the subject are taken into account by the systems and methods in order to determine product preferences and/or product recommendations. In some embodiments, other factors of the subject, although optional, may be also taken into account while determining product preferences and/or product recommendations for a subject. These product preferences or recommendations can be presented to the subject, either automatically via a display device or with assistance from a product consultant.

To obtain the biometric data in some embodiments, the subject will be exposed to a number of stimuli, such as fragrance/scent stimuli. Biometric data will then be collected from the subject based on her response to this fragrance/scent stimuli. In some examples, the collected biometric data relates to a subject's Electrodermal Resistance (EDR) or Electrodermal Activity (EDA).

For example, in some embodiments, the systems and methods detect an electrodermal response based on the response to an olfactory stimulus. In this regard, the system and methods detect a real-time cognitive process associated with an olfactory stimulus; detect a variation in an electrical characteristics of the skin associated with a response to one or more fragrance accords; detect a skin conductance based on a response to an olfactory stimulus; detect a change in a skin potential associated with a response to an olfactory stimulus; or detect conductivity fluctuations indicative of a response to an olfactory stimulus.

In accordance with an aspect of the present disclosure, a system is provided that comprises in an embodiment a plurality of sensors configured to sense an electrodermal response of a subject based on a response to an olfactory stimulus, and one or more engines configured to: receive the electrodermal response of a subject as Galvanic Skin Response (GSR) signals; process the GSR signals to generate GSR data; and generate a product recommendation based at least on said GSR data.

In some embodiments, the one or more engines are housed in a mobile computing device.

In some embodiments, the generated GSR data is represented as an image.

In some embodiments, the one or more engines are further configured to generate preferred characteristic parameters of the olfactory stimulus based on the GSR data and to generate the product recommendation based on the preferred characteristic parameters.

In some embodiments, the one or more engines are configured to determine a product recommendation by comparing data indictive of the generated preferred characteristic parameters to product data accessible by the one or more engines.

In some embodiments, the olfactory stimulus is a fragrance and wherein the data indictive of the generated preferred characteristic parameters includes a fragrance profile.

In some embodiments, the fragrance profile is presented to the subject as the product recommendation.

In some embodiments, the generated preferred characteristic parameters represent notes of the fragrance In some of these embodiments, the product recommendation is generated by comparing the fragrance profile with a set of fragrance profiles representing, respectively, a set of fragrances, the set of fragrance profiles accessible by the one or more engines.

In some embodiments, the system further comprising a camara configured to capture data indicative of the emotional state of the subject based on the response to the olfactory stimulus, wherein the product recommendation is generated based at least on said GSR data and said data indicative of the emotional state of the subject.

In some embodiments, the one or more engines include processing circuitry configured to: detect a real-time cognitive process associated with an olfactory stimulus, detect a variation in an electrical characteristics of the skin associated with a response to one or more fragrance accords, detect a skin conductance based on a response to an olfactory stimulus, detect a change in a skin potential associated with a response to an olfactory stimulus, or detect conductivity fluctuations indicative of a response to an olfactory stimulus.

In some embodiments, the plurality of sensors and/or the one or more engines form a scent response unit includes processing circuitry configured to detect one of: a real-time cognitive process associated with an olfactory stimulus; a variation in an electrical characteristics of the skin associated with a response to one or more fragrance accords; detect a skin conductance based on a response to an olfactory stimulus; a change in a skin potential associated with a response to an olfactory stimulus; or conductivity fluctuations indicative of a response to an olfactory stimulus.

In some embodiments, the olfactory stimulus includes a scent. In some of these embodiments, the one or more engines form a perfume selection unit that includes one of the following: processing circuitry configured to generate one or more virtual instances of a fragrance subset based on at least one input associated with an electrodermal activity measurand; processing circuitry configured to generate one or more virtual instances of a fragrance subset based on at least one input associated with a sympathetic skin response; processing circuitry configured to generate one or more instances of a degree of desirability score or a likeability measure; processing circuitry configured to generate one or more instances of a scent strength; processing circuitry configured to generate one or more instances of aromatic compound concertation; or processing circuitry configured to generate one or more instances of base notes, top notes or middle notes in a fragrance composition.

In accordance with another aspect of the present disclosure, a system is provided that comprises a scent response unit and a perfume selection unit. In some embodiments, the scent response unit includes processing circuitry configured to detect an electrodermal response based on a response to an olfactory stimulus. In some embodiments, the perfume selection unit including processing circuitry configured to generate one or more virtual instances of a fragrance subset based on at least one input associated with the electrodermal response.

In some embodiments, the scent response unit includes processing circuitry configured to: detect a real-time cognitive process associated with an olfactory stimulus; detect a variation in an electrical characteristics of the skin associated with a response to one or more fragrance accords; detect a skin conductance based on a response to an olfactory stimulus; detect a change in a skin potential associated with a response to an olfactory stimulus; or detect conductivity fluctuations indicative of a response to an olfactory stimulus.

In some embodiments, the perfume selection unit further includes one of: processing circuitry configured to generate one or more virtual instances of a fragrance subset based on at least one input associated with an electrodermal activity measurand; processing circuitry configured to generate one or more virtual instances of a fragrance subset based on at least one input associated with a sympathetic skin response; processing circuitry configured to generate one or more instances of a degree of desirability score or a likeability measure; processing circuitry configured to generate one or more instances of a scent strength; processing circuitry configured to generate one or more instances of aromatic compound concertation; or processing circuitry configured to generate one or more instances of base notes, top notes or middle notes in a fragrance composition.

In accordance with another aspect of the present disclosure, a method is provided for recommending a product to a subject. In an embodiment, the method includes obtaining Galvanic Skin Response (GSR) data of a subject based on exposure to an olfactory stimulus, analyzing the GSR data; and recommending a product to the subject based on at least the analyzed GSR data.

In some embodiments, recommending a product to the subject based on the analyzed GSR data includes either presenting a fragrance name to the subject or presenting a fragrance profile to the subject.

In some embodiments, the method further comprises obtaining questionnaire data of the subject indicative of a preference of a characteristic parameter of a product. In some embodiments, the recommendation of the product to the subject is based on the analyzed biometric data and the questionnaire data.

In some embodiments, the olfactory stimulus is a scent, and wherein the product is a perfume.

In some embodiments, recommending a product includes generating a fragrance profile based on the GSR data and presenting the fragrance profile to the subject.

In some embodiments, recommending a product includes generating a fragrance profile based on the GSR data, comparing the fragrance profile with a set of fragrance profiles representing, respectively, a set of fragrances to select a fragrance from the set of fragrances having a fragrance profile most similar to the generated fragrance profile, and presenting the selected fragrance to the subject.

In some embodiments, the method further comprises obtaining data indicative of the emotional state of the subject based on the exposure to the olfactory stimulus. In some embodiments, the recommendation of the product to the subject is based on the analyzed GSR data and said data indicative of the emotional state of the subject.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of the disclosed subject matter will become more readily appreciated as the same become better understood by reference to the following detailed description, when taken in conjunction with the accompanying drawings, wherein.

DETAILED DESCRIPTION

Figure 1:
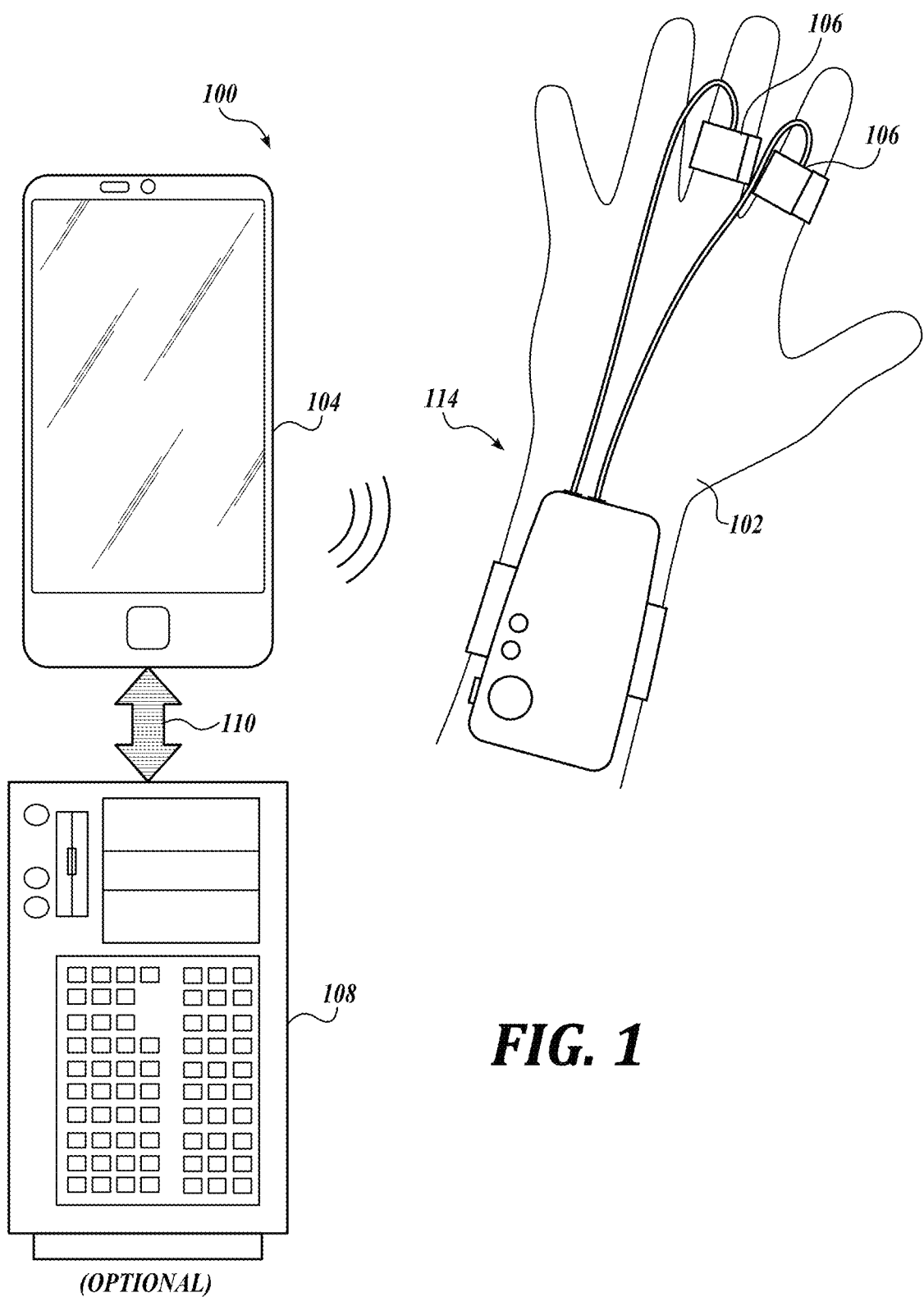
FIG. 1 is a schematic diagram that illustrates a non-limiting example of a system for generating and providing product, such as fragrance, recommendations to a subject according to an aspect of the present disclosure.

In order to provide recommendations for cosmetics, most existing techniques merely attempt to directly discern a subject's product preferences. Some techniques may attempt to determine a subject's product preferences based on the subject's stated preferences for a characteristic of the product, such as smell, color, finish, feel, etc. However, this technique produces sub-optimal recommendations, at least because only explicitly stated subject preferences are taken into account. Even in the presence of explicitly stated subject preferences, other factors (e.g., physical reactions (subconscious or conscious), personality traits, etc.), may also influence what products a given subject will prefer.

In that regard, in some embodiments of the present disclosure, biometric data of the subject are taken into account while determining product preferences and/or product recommendations. For example, physiological response data can be collected and used for determining product recommendations. In other embodiments, other factors of the subject, although optional, may be also taken into account while determining product preferences and/or product recommendations for a subject. These product preferences or recommendations are then represented to the subject, either automatically via a display device or with assistance from a product consultant.

The examples described throughout the disclosure relate to recommendations for a fragrance, such a perfume or cologne. It will be appreciated that the techniques and methodologies of the present disclosure transcend product types, and thus, can be used to provide recommendations to the subject for products other than fragrances.

In the examples described below, a subject will be exposed to a number of fragrance/scent stimuli. Biometric data will then be collected from the subject based on her physiological response to this fragrance/scent stimuli. In some embodiments, the collected biometric data relates to a subject's Electrodermal Resistance (EDR) or Electrodermal Activity (EDA). For example, a change in galvanic skin response (GSR) activity in response to a stimulus is referred to as an Event-Related Skin Conductance Response (ER-SCR), and can provide information about emotional arousal to the stimulus. Also, as may be used in the following, an event-related potential is the measured brain response resulting from a specific sensory, cognitive, or motor event.

With this biometric data, a computer system will, for example, recommend either a specific fragrance or will develop a fragrance profile from which a recommendation can be made with the assistance of, for example, a technician or fragrance consultant. In other embodiments, the computer system will use the biometric data in conjunction with optional data, such as data obtained from a questionnaire, image data of the subject referred later in the description as facial data, historical purchase data of the subject, etc., in order to present a product recommendation to the subject.

In some embodiments described herein, fragrances/scents presented to the subject may include two or more notes of an accord. Generally, an accord is a scent made up of several perfume notes, ingredients, etc., that blend together to form a distinct fragrance. For example, an accord usually includes a number of notes. Notes are descriptors of scents that can be sensed, and include base notes, middle or heart notes, and top or head notes.

These scent descriptors or notes are well known and widely use to describe the odor character (e.g., a characteristic parameter) of a fragrance.

Figure 8:
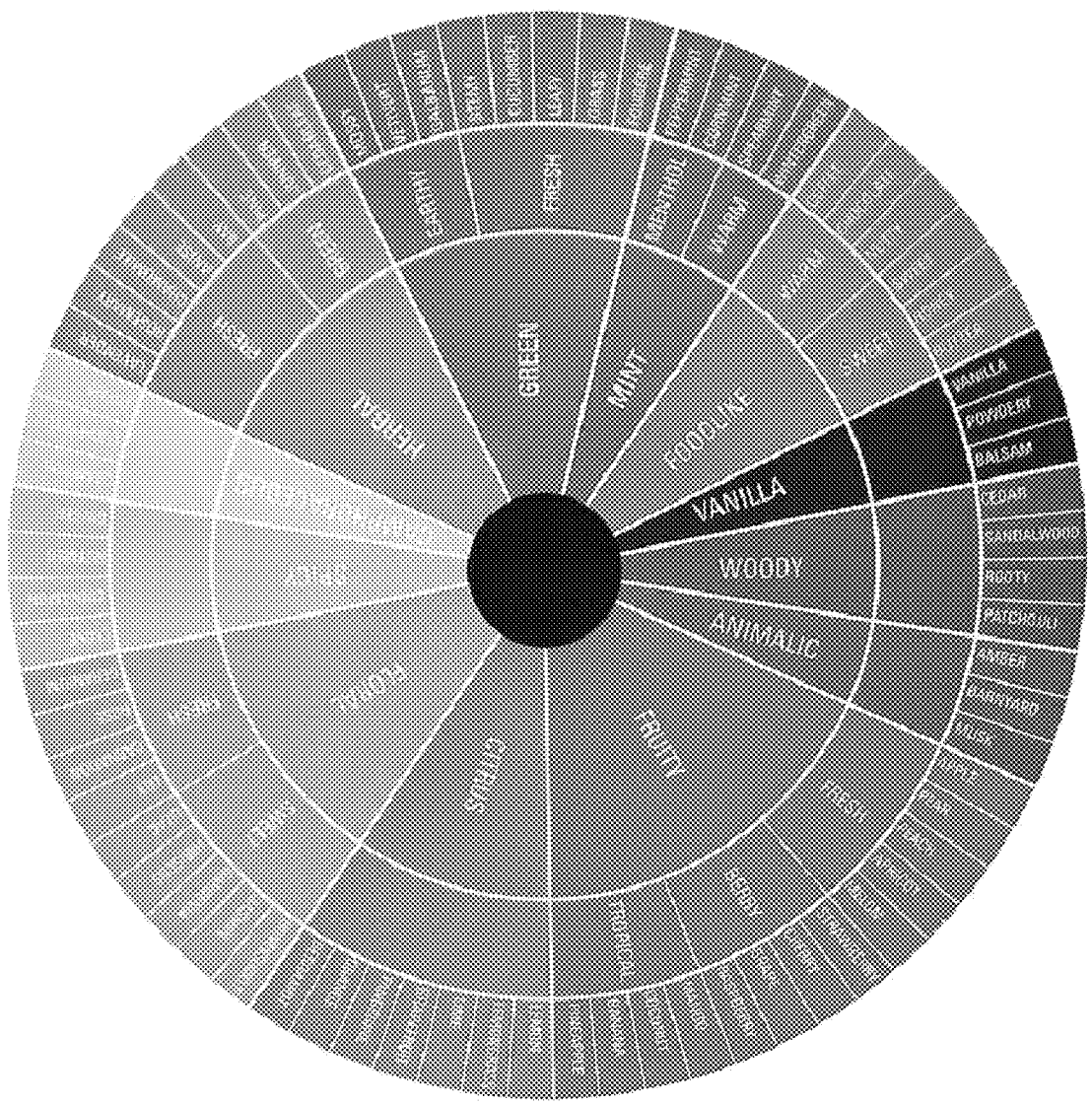
FIG. 8 is an example of a fragrance wheel.

Notes are typically chosen from fragrance families. Generally, fragrance families can be visually presented by a fragrance wheel. One example of a fragrance wheel is shown in FIG. 8. A fragrance wheel is a round diagram showing the inferred relationships among olfactory groups based upon similarities and differences in their odor. The groups bordering one another are implied to share common olfactory characteristics. Fragrance wheels are frequently used as a classification tool in oenology and perfumery.

Turning now to FIG. 1, there is shown a schematic diagram that illustrates a non-limiting example of a system 100 according to an aspect of the present disclosure. In the illustrated system, electrical characteristics or conductance of the skin of a subject 102 is measured using physical collection devices 106, such as Galvanic Skin Response (GSR) sensors, in response to a subject's exposure to a stimulus, such as a fragrance. As shown, a pair of physical collection devices 106 are placed on adjacent fingers of the subject's hand in order to measure skin conductivity between the pair of physical collection devices 106. In some embodiments, other parameters of the subject 102 can be monitored, such as Photoplethysmogram (PPG) signals for sensing heat rate via an optional pulse probe (not shown), eye movement, body movement, facial expressions, etc.

Still referring to FIG. 1, a mobile computing device 104 is coupled to the physical collection devices 106 in a wired or wireless manner to collect the skin conductance signals, such as GSR signals, generated by the physical collection devices 106. In some embodiments, the mobile computing device 104 is used to process the collected signals, and based on the processed signals, determines a product recommendation to be presented to the subject 102. In other embodiments, the mobile computing device 104 develops a fragrance profile based on the processed signals, from which a recommendation can be made with the assistance of, for example, a technician or fragrance consultant.

Figure 9:
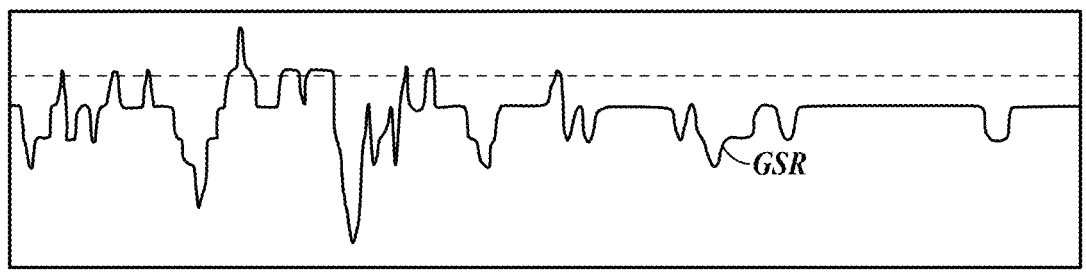
FIG. 9 is one example of a skin conductance graph or GSR graph generated as a result of processing collected GSR signals in accordance with the present disclosure.

In an embodiment, processing the collected GSR signals includes generating a skin conductance graph or GSR graph, such as the example shown in FIG. 9. The GSR graph can then be used by the mobile computing device 104 to recommend a product for the subject or present a fragrance profile that can aid the subject in product selection. Of course, the mobile computing device 104 can utilize the collected skin conductance signals in other ways, including via non-graphical processing techniques, in order to provide a product recommendation to the subject.

The mobile computing device 104 in other embodiments may transmit the GSR signals (processed or not) as GSR data to an optional server computing device 108 via a network 110. In some embodiments, the network 110 may include any suitable wireless communication technology (including but not limited to Wi-Fi, WiMAX, Bluetooth, 2G, 3G, 4G, 5G, and LTE), wired communication technology (including but not limited to Ethernet, USB, and FireWire), or combinations thereof.

With the GSR data received from the mobile computing device 104, the server computing device 108 may respond back to the mobile computing device 104 with a product recommendation to be presented to the subject 102. In other embodiments, the server computing device 108 may develop a fragrance profile from the GSR data. The fragrance profile can then be transmitted to the mobile computing device 104. Once received by the mobile computing device 104, a recommendation can be made with the assistance of, for example, a technician or fragrance consultant. Of course, in some embodiments, the server computing device 108 can access via the network 110 a cloud based computer processing system (not shown) to augment its processing, analyzing, generating, etc., capabilities.

In some embodiments, the server computing device 108 processes the GSR data and generates a GSR graph. The GSR graph can then be used by server computing device 108 to provide a product recommendation to the mobile computing device 104 for presentation to the subject 102. Alternatively, the generated GSR graph or the underlying data is transmitted to the mobile computing device 104 for use by the mobile computing device 104 for providing a product recommendation to the subject 102. Again, the mobile computing device 104 or the server computing device 108 can utilize the collected skin conductance signals in other ways, including via non-graphical processing techniques, in order to provide a product recommendation to the subject.

In some embodiments, the mobile computing device 104 may also be used to present an optional questionnaire to the subject 102. The questionnaire may include questions that allow preferences of the subject 102 to be determined. In some embodiments, the questionnaire may also allow at least one personality trait to be determined. For example, in some embodiments, a personality trait can be correlated to one or more fragrance preferences, etc.

In some embodiments, the questionnaire can be served to the mobile computing device 104 by the optional server computing system 108 for presentation to the subject 102. In other embodiments, the mobile computing device 104 can generate and present the questionnaire to the subject.

In some embodiments, the responses to the questionnaire are received and processed locally by the mobile computing device 104. In other embodiments, the responses received by the mobile computing device 104 are sent to the optional server computing system 108 for processing. Of course, in some embodiments, the server computing device 108 can access via the network 110 a cloud based computer processing system (not shown) to augment its processing capabilities.

In any case, processed responses to the questionnaire may be used by either the mobile computing device 104 or the server computing device 108 in conjunction with the GSR signals collected from the subject for providing, for example, a product recommendation.

In some embodiments, one or more images can be captured by the mobile computing device 104 while the questionnaire is being conducted and/or during stimulus exposure. The collected images, such as video, can be analyzed for determining, for example, an emotional state of the subject 102. In some embodiments, the results can be employed, for example, to augment the biometric data or to verify the results of the questionnaire responses when generating the product recommendation.

Figure 10:
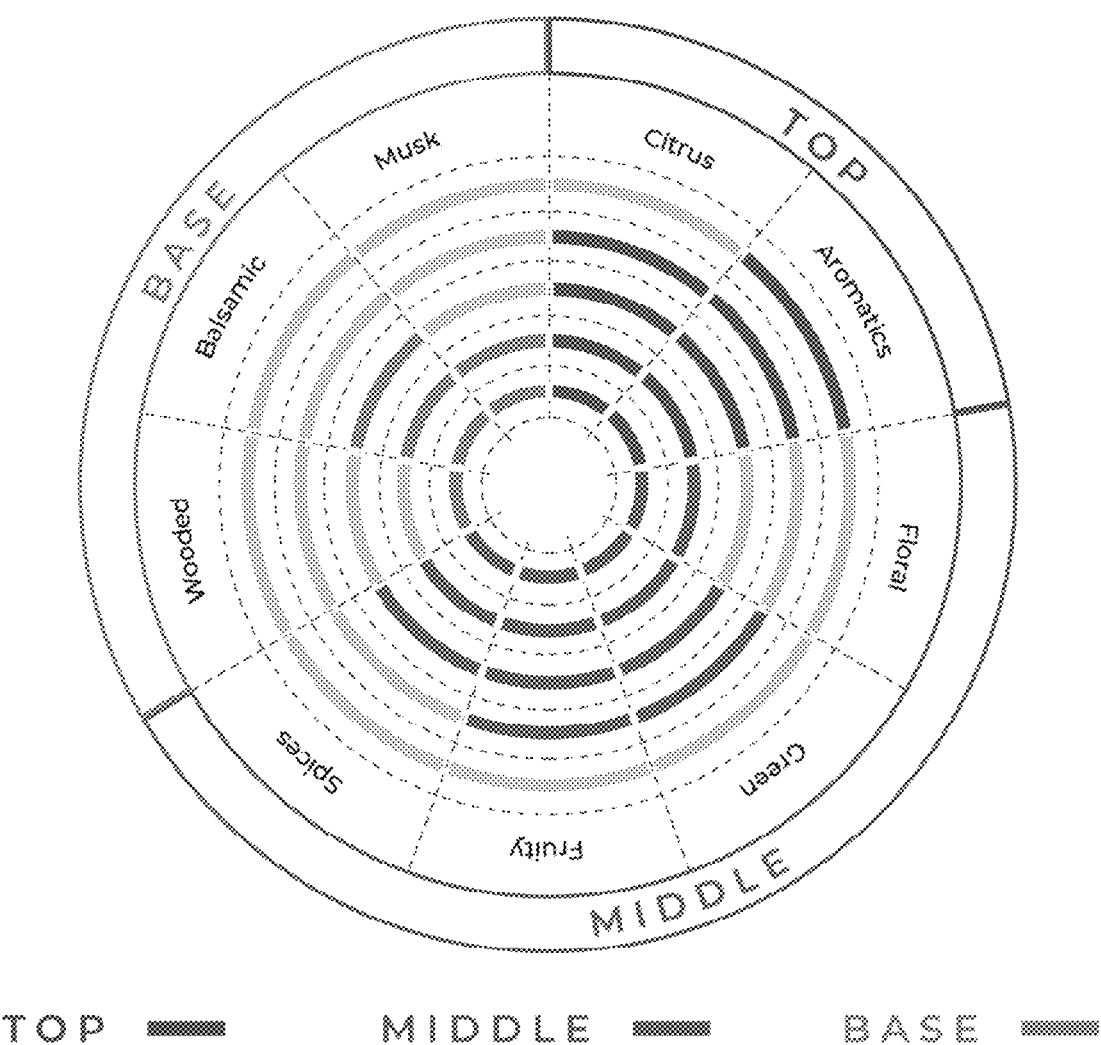
FIG. 10 is one example of a note diagram generated by the system and presented to the subject in accordance with an aspect of the present disclosure.

In some embodiments, the product recommendation may be provided to the subject 102 in a convenient, simple format. For example, the product recommendation can be a specific fragrance, e.g., identified by a tradename such as Trade Winds. Other information about the subject 102, such as scent preferences, a personality trait, prior fragrance purchases, etc., may be also presented to the subject. Additionally or alternatively, the product recommendation may take the form of a fragrance profile. The fragrance profile can be presented as a word-based description or visually depicted as a note diagram. One example of a note diagram generated by the system 100 and presented to the subject 102 is shown in FIG. 10. With the word-based description or the note diagram, a fragrance having a high probability of enjoyment by the subject can be selected, either independently or with the assistance of a fragrance consultant.

Figure 2:
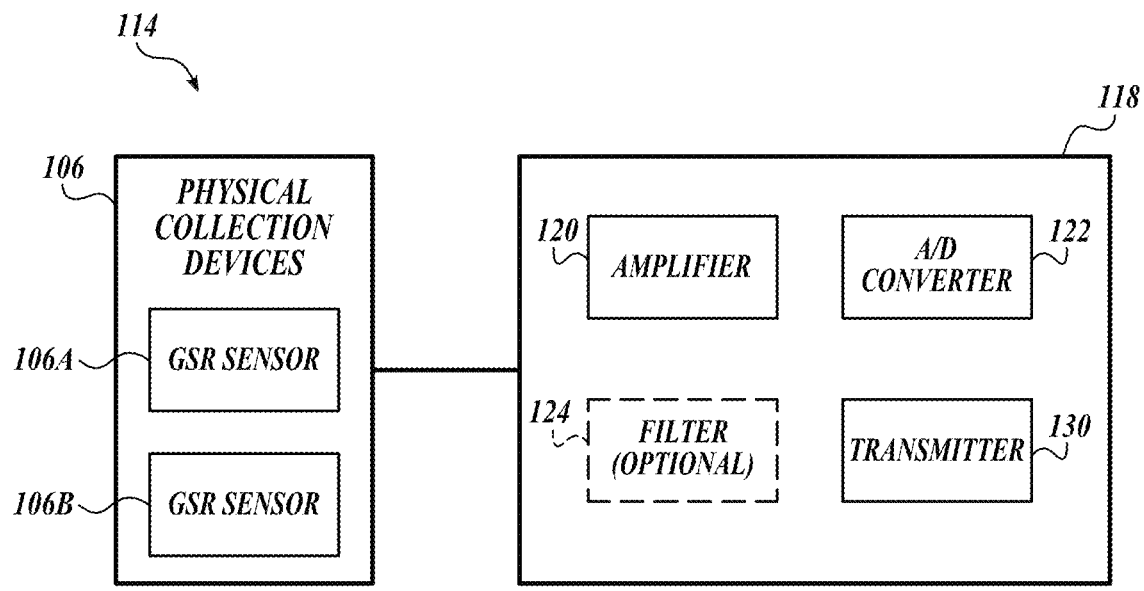
FIG. 2 depicts one example of a GSR unit suitable for use in the system of FIG. 1.

FIG. 2 is a block diagram that illustrates various components of a non-limiting example of GSR unit 114 according to an aspect of the present disclosure. The GSR unit 114 includes a pair of physical collection devices 106 in the form of GSR sensors ("GSR sensors 106") and a process and transmit circuit 118. Either dry or gel electrodes can be employed with embodiments of the present disclosure.

Generally, GSR electrodes detect the changes in electrical (ionic) activity of the skin as a result from changes in sweat gland activity. The GSR sensors 106, sometimes referred to as GSR electrodes, are configured to measure these changes, usually as skin conductance measurements, sometimes referred to as GSR signals. The GSR signals measured by the GSR sensors 106 can be suitably processed for transmission to the mobile computing device 104 for storage, data processing and/or analysis, etc. For example, the GSR signals in some embodiments are amplified by an amplifier 120 and digitized by an A/D converter 122 prior to arrival at transmitter 130. In some embodiments, the GSR signals can be filtered in the analog domain prior to conversion by the A/D converter 122 or in the digital domain after conversion by the A/D converter 122 via one or more filters 124.

One non-limiting example of a GSR unit 114 that outputs suitable signals for use by the system 100 is the Shimmer3 GSR+unit from Shimmer. Other GSR devices can also be used.

Figure 3:
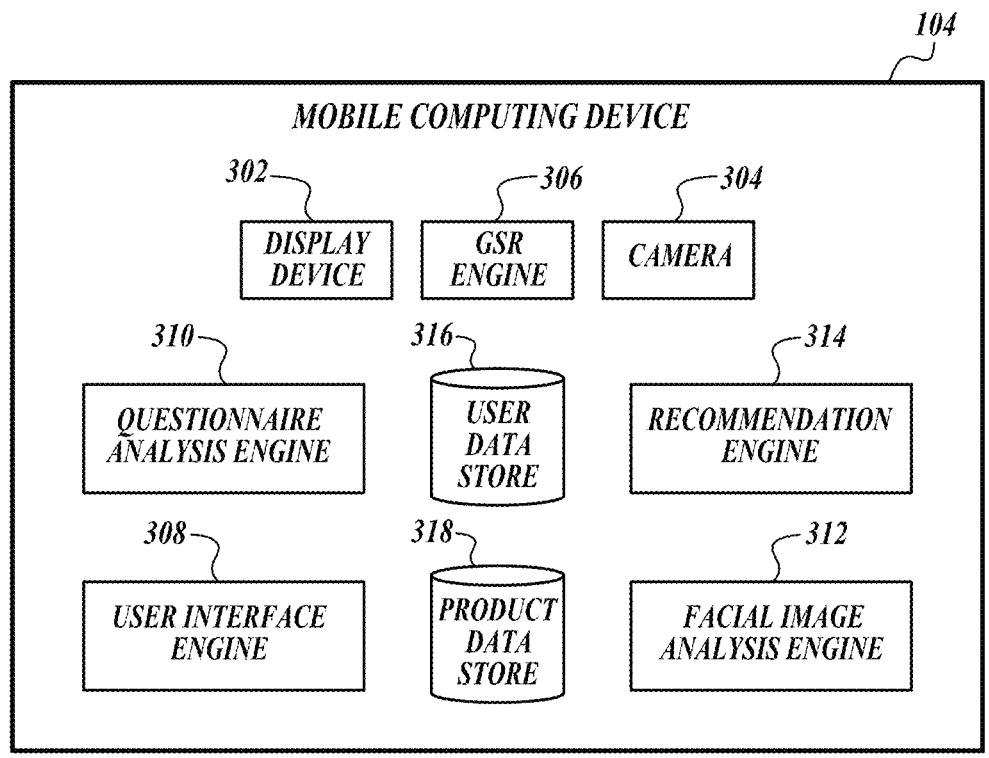
FIG. 3 is a block diagram that illustrates a non-limiting example of a mobile computing device suitable for use in the system of FIG. 1.

FIG. 3 is a block diagram that illustrates various components of a non-limiting example of a mobile computing device 104 according to an aspect of the present disclosure. The mobile computing device 104 is configured to collect information from a subject 102 that reflects a physiological response (e.g., eccrine activity) based on exposure to one or more fragrances in, for example, a sequential order. In particular, the mobile computing device 104 is configured to receive GSR signals from one or more GSR sensors 106 for processing, recordation, transmission (optional) and/or analysis (optional). In some embodiments, the mobile computing device 104 is configured to receive GSR signals from the transmitter 130 of the unit 114 (see FIG. 2).

In some embodiments, the mobile computing device 104 processes the GSR signals for use in determining a product recommendation for the subject 102. In other embodiments, as will be described in more detail below, the GSR signals (processed or not) are transmitted as GSR data to the optional server computing system 108 via the network 110 for processing and/or generating a product recommendation, etc. In either case, the mobile computing device 104 can then present the product recommendation to the subject 102, or to a cosmetic consultant that is assisting the subject 102. In some embodiments, generating a product recommendation can be the identification of a specific product (e.g., a specific perfume/cologne). In other embodiments, generating a product recommendation can be information, such as a fragrance profile, that assists in the selection of a specific product or product family.

In some embodiments, the mobile computing device 104 may be a smartphone. In some embodiments, the mobile computing device 104 may be any other type of computing device having the illustrated components, including but not limited to a tablet computing device or a laptop computing device. In some embodiments, the mobile computing device 104 may not be mobile, but may instead be a stationary computing device such as a desktop computing device or computer kiosk. In some embodiments, the illustrated components of the mobile computing device 104 may be within a single housing. In some embodiments, the illustrated components of the mobile computing device 104 may be in separate housings that are communicatively coupled through wired or wireless connections (such as a laptop computing device with an external camera connected via a USB cable). The mobile computing device 104 also includes other components that are not illustrated in FIG. 3, including but not limited to one or more processors, a non-transitory computer-readable medium, a power source, and one or more network communication interfaces.

In order to implement some (or all) of the technology and methodology set forth herein, the mobile computing device 104 includes, in some embodiments for example, a display device 302, a camera 304, a GSR engine 306, a user interface engine 308, an optional questionnaire analysis engine 310, an optional facial image analysis engine 312, a recommendation engine 314, a user data store 316 and a product data store 318. Each of these components will be described in turn.

In some embodiments, the display device 302 is any suitable type of display device, including but not limited to an LED display, an OLED display, or an LCD display, that is capable of presenting interfaces to the subject 102. As will be described in more detail below, such interfaces include a questionnaire, a product recommendation, etc., to be presented to the subject 102. In some embodiments, the display device 302 may include an integrated touch-sensitive portion that accepts input from the subject 102.

In some embodiments, the camera 304 is any suitable type of digital camera that is used by the mobile computing device 104 for capturing images, such as video. In some embodiments, the mobile computing device 102 may include more than one camera 304, such as a front-facing camera and a rear-facing camera.

In some embodiments, the GSR engine 306 is configured to collect GSR signals from the GSR sensors 106, process the GSR signals, and record the GSR signals in a time-based manner as GSR data in the user data store 314. In some embodiments, processing the GSR signals may include but is not limited to converting, filtering, transforming, and/or the like. The GSR engine 306 is also configured to process the signals in order to generate a GSR graph, such as the example shown in FIG. 9.

In some embodiments, the user interface engine 308 is configured to present a user interface on the display device 302. In some embodiments, the user interface engine 308 is configured to present a product recommendation, such as a name of a product or a fragrance profile to the user 102. In some embodiments, the user interface engine 308 may be configured to present visualizations of the GSR data as a GSR graph on the display device 302. In some embodiments, the user interface engine 308 may be configured to use the camera 304 to capture images of the subject 102 during the questionnaire and/or fragrance stimulus process.

Figure 11:
FIG. 11 illustrates an example of a question, depicting one or more scenes, that is generated by the user interface engine and presented to the subject.

In some embodiments, the user interface engine 308 may be optionally configured to present on the display device 302 at least one questionnaires to the subject 102 for collecting information from the subject 102. In some embodiments, the questionnaire aims to collect information that may be relevant to the characteristic parameters of the fragrances to which the subject was or will be exposed. For example, the questionnaire may ask via a series of true/false or multiple choice questions that may elicit preferences to certain head, middle, or base notes. For example, one question of the questionnaire, which is shown in FIG. 11, may present to the subject a number of pictures depicting scenes, such as the beach, the forest, etc., to elicit a response to which depicted scene is associated with a preferred fragrance of the subject. In another question of the questionnaire, the subject may be asked whether they prefer feminine, masculine or unisex scents. In yet another question of the questionnaire, the subject may be asked whether they prefer the scent to be perceivable, subtle, complimentary or strong. In yet another question of the questionnaire, the subject may be asked to enter her preferred fragrances, including the most recently purchased fragrance. Some or all of the collected data can be stored, for example, in the user data store 316.

In some embodiments, the questionnaire analysis engine 310 may be configured to receive responses to the questionnaire from the subject 102 via the user interface engine 308, and may determine at least one preference, e.g., scent preference, scent characteristic, etc., of the subject 102 based on one or more of the responses. For example, if the subject 102 chose the scene of the forest as preferred, the questionnaire analysis engine 310 may be configured to determine that the subject 102 prefers woody notes, as shown for example in the fragrance wheel of FIG. 8. In some embodiments, the questionnaire analysis engine 310 may be configured to compare the responses to data stored, for example, in the product data store 318. In an embodiment, the questionnaire analysis engine 310 may be configured to determine at least one personality trait of the subject 102 based on one or more of the responses.

In some embodiments, the facial image analysis engine 312 is configured to analyze images (e.g., video) captured by the camera 304. For example, in some embodiments, the facial image analysis engine 312 includes one or more image processing algorithms that analyze video captured by the camera 304 for determining facial expressions, head movement, eye tracking, etc., of the subject 102. The images captured by the camera during use of the system 100 can be referred to as facial data.

In some embodiments, the recommendation engine 314 may be configured to generate at least one product recommendation for the subject 102 based at least on the GSR data. In other embodiments, the recommendation engine 314 may be configured to generate at least one product recommendation for the subject 102 based at least on the GSR data and the optional questionnaire data. In yet other embodiments, the recommendation engine 314 may be configured to generate at least one product recommendation for the subject 102 based at least on the GSR data, the optional questionnaire data, and/or the data processed by the facial analysis engine 312.

In some embodiments, the product recommendation is in the form of a specific product, such as Trade Winds branded perfume. In other embodiments, the product recommendation is in the form of a fragrance profile. In these embodiments, the fragrance profile can be presented as a word-based description, visually depicted as a note diagram, etc. In some embodiments, the recommendation engine 314 provides the product recommendation to be presented to the subject 102 via the display device 302.

For example, FIG. 10 is one example of a fragrance note diagram that can be generated by the recommendation engine 314 and presented to the subject 102. The note diagram depicts characteristic parameters of the fragrances preferred by the subject 102. As shown in FIG. 10, the note diagram depicts visually the top notes, the heart or middle notes, and optionally, the base notes, that are preferable to the subject. These notes are represented in a pattern of that form a wheel, with bar segments indicating strength of preference. For example, regarding the top notes, aromatics is depicted as five (5) bars, which the subject prefers more than floral, which is depicted as one (1) bar. Similarly, regarding the middle notes, fruity is depicted as four (4) bars, which the subject prefers more than spices, which is depicted as three (3) bars. In addition to or in the alternative to the number of bars, the color of the bars may also indicate strength of enjoyment. In some embodiments of the note diagram, the strength values may be linear (i.e., two bars is twice as preferable as one bar, etc.) or non-linear, such as Logarithmic, exponential, etc.

In the diagram depicted in FIG. 10, this subject enjoys aromatics, and to a lesser extent citrus, in the top notes, green and fruity, and to a lesser extent spices, in the middle notes, and balsamic, and to a lesser extent musk or wooded, in the base notes. In some embodiments, this note diagram can be presented on the display device 302 via user interface engine 308. In some embodiments, the note diagram can be used by a fragrance consultant to recommend a product type or product line that corresponds to the note profile of the note diagram. In other embodiments, the note diagram can be used by the subject 102 to compare to a fragrance chart of one or more fragrance sellers. In yet other embodiments, the recommendation engine 314 can analyze, for example, the image of the note diagram or the underlying data used to generate the note diagram, and based on the analysis, automatically present a product recommendation to the subject 102.

In some embodiments, the recommendation engine 314 employs one or more algorithms for analyzing the images (e.g., the GSR graph, etc.) generated from the biometric data. Based on this analysis, one or more characteristic parameters of the fragrances preferred by the subject 102 can be determined. For example, an increase in sweat produced by the subject 102 during exposure to the fragrance(s) causes skin conductance to change. This change can be correlated to a positive stimuli (e.g. happiness or enjoyment of the fragrance), a negative stimuli (e.g. sadness or threat of the fragrance), or to the characteristic parameters (note profiles) thereof. Thus, the stimuli (e.g., fragrance) can result in an increase in arousal, and thus, in an increase in skin conductance. The GSR signals represent the intensity of the emotion felt by the subject 102 based on exposure to the stimuli.

In some embodiments, the preferred characteristic parameters of the fragrance are determined based on the image(s) of the GSR data. For example, in some embodiments, image processing techniques are applied to the images in order to determine the preferred characteristic parameters of the fragrances. In some embodiments, the recommendation engine 314 may comprise or access an artificial neural network that is trained to determine the characteristic parameters based on the images. Of course, any other type of suitable machine learning technique and/or classical image processing technique may be performed in order to determine the preferred characteristic parameters of the fragrances exposed to the subject 102.

For example, in some embodiments, the recommendation engine 314 includes a machine learning model for assisting in determining the product recommendation. The machine learning model can be trained using, for example, images of GSR graph, etc., of subjects exposed to known fragrances (with known characteristic parameters, such as note profiles) that resulted in positive emotion (e.g., enjoyment) and negative emotion (e.g., dislike or sadness) by the subject 102. In some embodiments, the images from known fragrances are used to create a set of supervised training data, and a machine learning model such as an artificial neural network may be trained with the training data using any suitable technique, including but not limited to gradient descent. The resulting machine learning model will accept an image from the GSR engine 306 as input, and will output either preferred characteristic parameters or a product recommendation that has a high probability of enjoyment by the subject 102. In some embodiments, the preferred characteristic parameters can be used to generate a fragrance profile, such as the note diagram of FIG. 10, of the subject 102.

In some embodiments, the processed data from the questionnaire analysis engine 310 and/or the facial analysis engine 312 can be used by the recommendation engine 314 to either augment the decisions made by the machine learning model or the signal processing carried out by the recommendation engine 314. In some embodiments, the analyzed data from the facial analysis engine 312 can be used to verify the responses to the questionnaire analyzed by the questionnaire analysis engine 310 and vice versa.

Accordingly, with the knowledge of the preferred characteristic parameters of the fragrances determined from the GSR data, and/or the questionnaire data (optional) and facial data (optional), the recommendation engine 314 is configured to determine an appropriate product stored in a product data store 318 that matches or is highly correlative to the preferred characteristic parameters determined by the system 100. For example, the recommendation engine 314 can compare the results to a product (e.g., fragrance, etc.) map, a look-up table, etc., stored in the product data store 318. The comparison can be based, for example, on a potential match confidence level.

In some embodiments, the mobile computing device 104 may also include a user data store 316, which is configured to store records for each subject 102 that uses the system 100. The records may include, for example, at least one fragrance product, at least one fragrance profile, responses to a questionnaire, at least one personality trait, at least one product recommendation, facial data, and/or other information collected or determined by the system 100. In an embodiment, feedback received from the subject 102 after having used the recommended product(s) may also be stored in the user data store 316 or forward to the product data store 318 in order to improve future product recommendations by the system 100.

Further details about the actions performed by each of these components are provided below.

"Engine" refers to logic embodied in hardware or software instructions, which can be written in a programming language, such as C, C++, COBOL, JAVA™, PHP, Perl, HTML, CSS, JavaScript, VBScript, ASPX, Microsoft .NET™, Go, and/or the like. An engine may be compiled into executable programs or written in interpreted programming languages. Software engines may be callable from other engines or from themselves. Generally, the engines described herein refer to logical modules that can be merged with other engines, or can be divided into sub-engines. The engines can be stored in any type of computer-readable medium or computer storage device and be stored on and executed by one or more general purpose computers, thus creating a special purpose computer configured to provide the engine or the functionality thereof. In some embodiments, the engines can be implemented by one or more circuits, programmable processors, application specific integrated circuits (ASICs), programmable logic devices (PLDs) and/or field programmable logic devices (FPLDs), etc.

"Data store" refers to any suitable device configured to store data for access by a computing device. One example of a data store is a highly reliable, high-speed relational database management system (DBMS) executing on one or more computing devices and accessible over a high-speed network. Another example of a data store is a key-value store. However, any other suitable storage technique and/or device capable of quickly and reliably providing the stored data in response to queries may be used, and the computing device may be accessible locally instead of over a network, or may be provided as a cloud-based service. A data store may also include data stored in an organized manner on a computer-readable storage medium, such as a hard disk drive, a flash memory, RAM, ROM, or any other type of computer-readable storage medium. One of ordinary skill in the art will recognize that separate data stores described herein may be combined into a single data store, and/or a single data store described herein may be separated into multiple data stores, without departing from the scope of the present disclosure.

Figure 4:
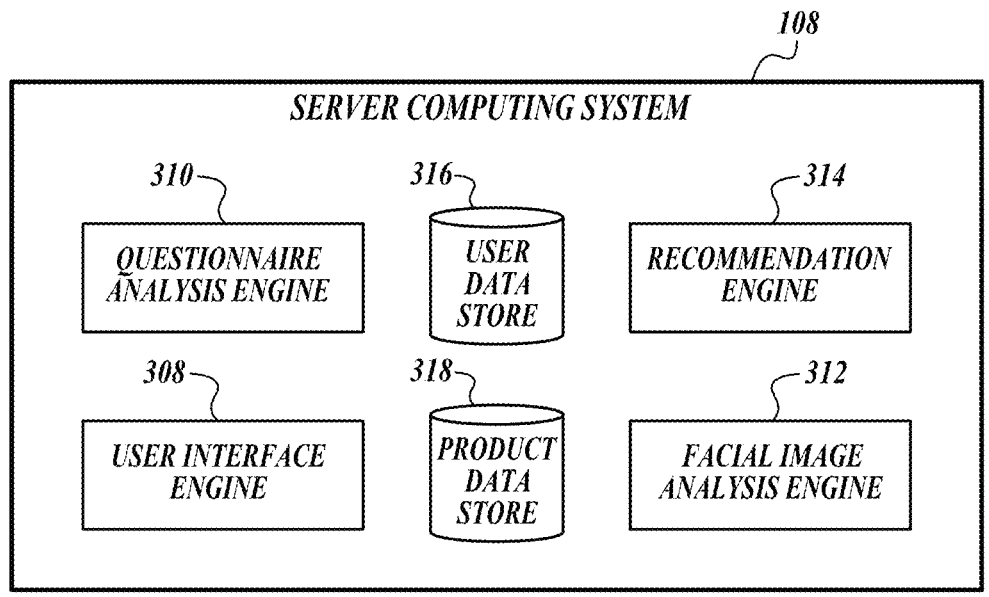
FIG. 4 is a block diagram that illustrates a non-limiting example of a server computing device suitable for use in the system of FIG. 1.

FIG. 4 is a block diagram that illustrates various components of a non-limiting example of an optional server computing system 108 according to an aspect of the present disclosure. In these embodiments, one or more functions of the mobile computing device set forth above can be additionally or alternatively carried out by the server computing device 108. For example, the fragrance preference information (e.g., scent preferences from, for example, biometric data (e.g., eccrine activity) from scent exposure, optional questionnaire data, and/or optional facial data) collected by the mobile computing device 104 can be transmitted, with or without additionally processing (e.g., filtering, transforming, etc.) and/or storage, to the server computing system 108 via the network 110. In that regard, the server computing system 108 can include, for example, the GSR engine 306 (FIG. 3) for processing and storing the GSR signals and optionally generating a GSR graph, such as the example shown in FIG. 9.

In some embodiments, the server computing system 108 uses the information received from the mobile computing device 104 to determine a product recommendation to be used by the subject 102, and transmits the recommendation back to the mobile computing device 104 for presentation to the subject 102. In that regards, the server computing system 108 can additionally or alternatively include the questionnaire analysis engine 310, the facial image analysis engine 312, the recommendation engine 314, and/or the product data store 318, the functionality of which was described in detail above. In some embodiments, the server computing system 108 may also include the user data store 316.

Figure 5:
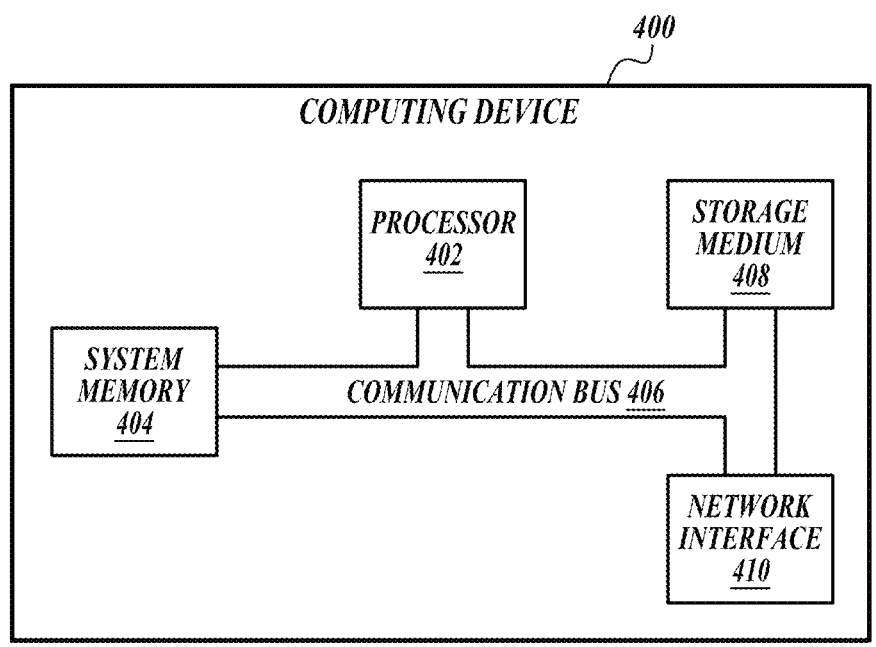
FIG. 5 is a block diagram that illustrates a non-limiting example of a computing device appropriate for use as a computing device with embodiments of the present disclosure.

FIG. 5 is a block diagram that illustrates aspects of a representative computing device 400 appropriate for use as a computing device of the present disclosure. While multiple different types of computing devices were discussed above, the representative computing device 400 describes various elements that are common to many different types of computing devices, such as the mobile computing device 104 and/or the server computing device 108. While FIG. 5 is described with reference to a computing device that is implemented as a device on a network, the description below is applicable to servers, personal computers, mobile phones, smart phones, tablet computers, computer kiosks, embedded computing devices, and other devices that may be used to implement portions of embodiments of the present disclosure. Moreover, those of ordinary skill in the art and others will recognize that the computing device 400 may be any one of any number of currently available or yet to be developed devices.

In its most basic configuration, the computing device 400 includes at least one processing circuit, such as processor 402, and a system memory 404 connected by a communication bus 406. Depending on the exact configuration and type of device, the system memory 404 may be volatile or nonvolatile memory, such as read only memory ("ROM"), random access memory ("RAM"), EEPROM, flash memory, or similar memory technology. Those of ordinary skill in the art and others will recognize that system memory 404 typically stores data and/or program modules that are immediately accessible to and/or currently being operated on by the processor 402. In this regard, the processor 402 may serve as a computational center of the computing device 400 by supporting the execution of instructions.

As further illustrated in FIG. 5, the computing device 400 may include a network interface 410 comprising one or more components for communicating with other devices over a network. Embodiments of the present disclosure may access basic services that utilize the network interface 410 to perform communications using common network protocols. The network interface 410 may also include a wireless network interface configured to communicate via one or more wireless communication protocols, such as WiFi, 2G, 3G, LTE, WiMAX, Bluetooth, Bluetooth low energy, and/or the like. As will be appreciated by one of ordinary skill in the art, the network interface 410 illustrated in FIG. 5 may represent one or more wireless interfaces or physical communication interfaces described and illustrated above with respect to particular components of the computing device 400.

In the exemplary embodiment depicted in FIG. 5, the computing device 400 also includes a storage medium 408. However, services may be accessed using a computing device that does not include means for persisting data to a local storage medium. Therefore, the storage medium 408 depicted in FIG. 5 is represented with a dashed line to indicate that the storage medium 408 is optional. In any event, the storage medium 408 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer readable instructions, data structures, program modules, or other data. In this regard, the system memory 404 and storage medium 408 depicted in FIG. 5 are merely examples of computer-readable media.

Suitable implementations of computing devices that include a processor 402, system memory 404, communication bus 406, storage medium 408, and network interface 410 are known and commercially available. For ease of illustration and because it is not important for an understanding of the claimed subject matter, FIG. 5 does not show some of the typical components of many computing devices. In this regard, the computing device 400 may include input devices, such as a camera, keyboard, keypad, mouse, microphone, touch input device, touch screen, tablet, and/or the like. Such input devices may be coupled to the computing device 400 by wired or wireless connections including RF, infrared, serial, parallel, Bluetooth, Bluetooth low energy, USB, or other suitable connections protocols using wireless or physical connections. Similarly, the computing device 400 may also include output devices such as a display, speakers, printer, etc. Since these devices are well known in the art, they are not illustrated or described further herein.

In some embodiments, the plurality of sensors and/or the one or more engines form a scent response unit. In some embodiments, the scent response unit includes processing circuitry configured to detect one of: a real-time cognitive process associated with an olfactory stimulus; a variation in an electrical characteristics of the skin associated with a response to one or more fragrance accords; detect a skin conductance based on a response to an olfactory stimulus; a change in a skin potential associated with a response to an olfactory stimulus; or conductivity fluctuations indicative of a response to an olfactory stimulus.

In some embodiments, the one or more engines form a perfume selection unit that includes one of the following: processing circuitry configured to generate one or more virtual instances of a fragrance subset based on at least one input associated with an electrodermal activity measurand; processing circuitry configured to generate one or more virtual instances of a fragrance subset based on at least one input associated with a sympathetic skin response; processing circuitry configured to generate one or more instances of a degree of desirability score or a likeability measure;

processing circuitry configured to generate one or more instances of a scent strength; processing circuitry configured to generate one or more instances of aromatic compound concertation; or processing circuitry configured to generate one or more instances of base notes, top notes or middle notes in a fragrance composition.

Figure 6:
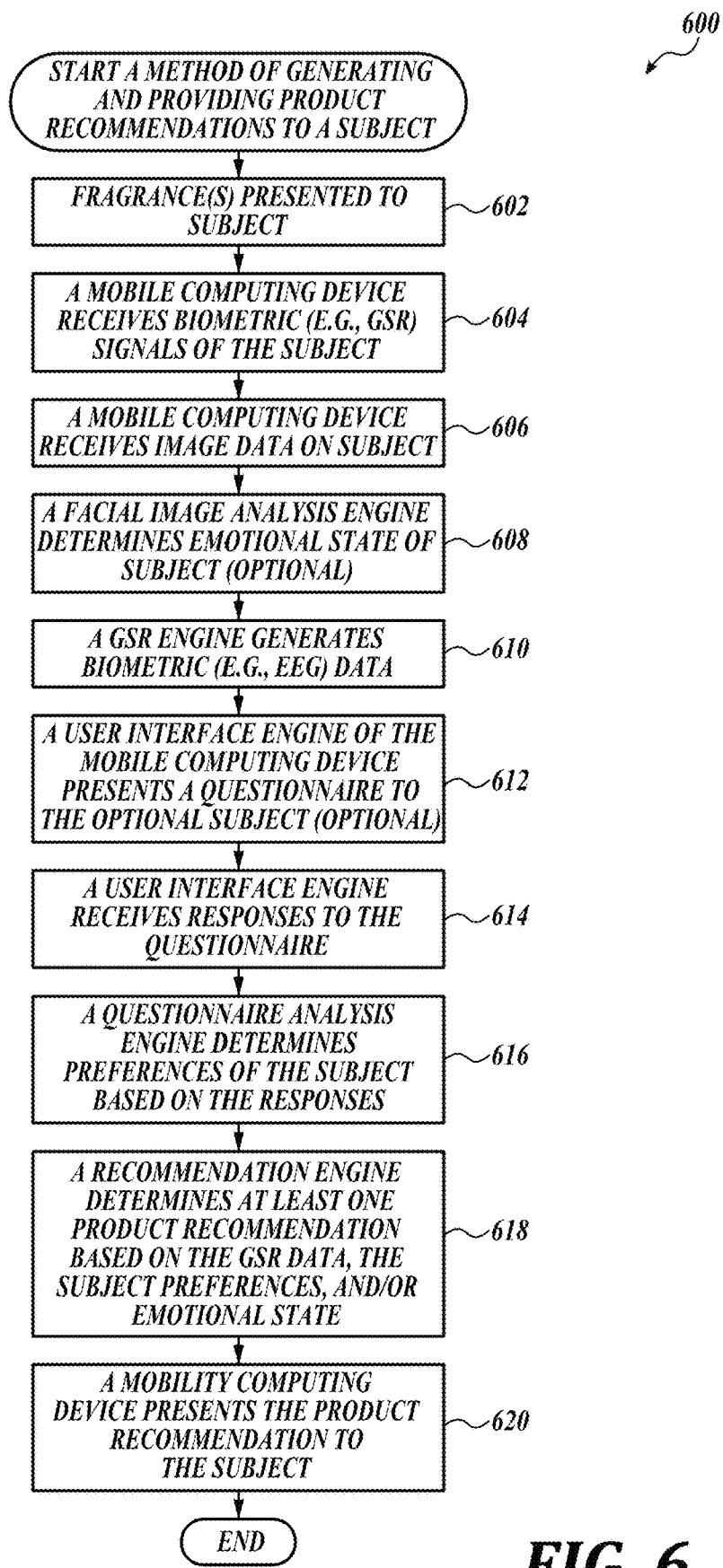
FIG. 6 is a flowchart that illustrates a non-limiting example of a method of generating and providing product recommendations to a subject according to an aspect of the present disclosure.

FIG. 6 is a flowchart that illustrates a non-limiting example of a method for generating and/or providing product recommendations to a subject according to one or more aspects of the present disclosure. The representative method, generally designated 600, will be described with references to one or more components of the system 100 depicted in FIGS. 1-5.

Prior to starting the method 600, one or more GSR sensors 106 are coupled to the subject 102. In some embodiments, two GSR sensors 106 are coupled to adjacent fingers of the subject's nondominant hand. If desired, other sensors can be attached to the subject 102, such as a heart rate sensor or the like.

Once the sensors 106 have been suitably associated with a hand of a subject 102, the method can begin. In some embodiments, as will be described below, images of the subject are captured by the mobile computing device 104 during use of the system 100. In these embodiments, the subject 102 and the mobile computing device 104 are arranged with respect to each other such that images from camera 304 can capture at least the face of the subject 102.

From a start block, the method 600 proceeds to block 602, where the subject 102 is exposed to one or more fragrances. For example, the subject is exposed to a sequence of fragrances. The subject 102 is exposed to each fragrance for a period of time. In an embodiment, the period of time is about 45 seconds. Of course, shorter or longer periods of time can be employed. In other embodiments, the period of time is about five (5) minutes or longer. In some embodiment, the fragrances exposed to the subject include at least two fragrance notes, such as the top and middle notes.

The subject's reaction to the one or more fragrances is captured by the GSR sensors 106 and transmitted as GSR signals to the mobile computing device 104. In that regard, the mobile device 104 is coupled in communication with the GSR sensors 106 and receives the GSR (e.g., biometric) signals of the subject 102 at block 604. In some embodiments, the subject's reaction to the one or more fragrances is also captured by the camera 304 of the mobile computing device 104 at block 606. Of course, the actions carried out at block 606 are optional.

At block 608, the facial image analysis engine 312 determines the emotional state of the subject 102 based on the images captured by the camera 304. For example, the facial image analysis engine 312 employs one or more algorithms to analyze the video captured by the camera during the time periods that the subject is exposed to the fragrances (or questionnaire described below). The one or more algorithms are configured, for example, to analyze the facial expressions of the subject and/or body movement or gestures of the subject in order to determine whether or not the subject 102 enjoyed (e.g. positive emotional response) the fragrance or disliked (e.g., negative emotional response) the fragrance.

In some embodiments, the video captured by the camera 304 is processed by the facial image analysis engine 312 residing on the mobile computing device 104. In other embodiments, the video is processed by facial image analysis engine 312 residing on the server computing device 108. In these or other embodiments, the video is stored in the user data store 316, either locally at the mobile computing device 104 or remotely at the server computing system 108.

At block 610, the GSR signals can be processed by the GSR engine 306 to generate, for example, GSR data. In some embodiments, the GSR signals are processed by the GSR engine 306 residing on the mobile computing device 104. In other embodiments, the GSR signals are processed by the GSR engine 306 residing on the server computing device 108. In these or other embodiments, the GSR data is stored in the user data store 314, either locally at the mobile computing device 104 or remotely at the server computing system 108.

In some embodiments, the actions performed at blocks 602-610 are repeated for each fragrance to be exposed to the subject 102. In other embodiments, the actions performed at blocks 602-606 can be performed for each fragrance prior to the actions performed at block 608 and 610. In an embodiment, the subject is exposed to four fragrances. Of course, a number of fragrances more or less than four can be used in embodiments of the present disclosure.

In one embodiment, a preselected set of fragrances are exposed to the subject 102. For example, the preselected set of fragrances can be the top four sellers in a company's line of fragrances. In other embodiments, as will be described in more detail with regard to FIG. 7, the reaction of the subject 102 to the preceding fragrance may be used by the system 100 to influence the choice of the subsequent fragrance(s) to be exposed to the subject 102. For example, the GSR data (e.g., the GSR graph) and/or the determined emotional state of the subject from exposure to a fragrance may be presented on the display device 302. With the aid of a fragrance consultant, the next fragrance can be chosen for exposure to the subject 102. Alternatively, the system 100 can be configured to automatically choose the next fragrance to be presented to the subject based on the reaction of the subject to the previous fragrance(s).

In some embodiments, each fragrance exposed to the subject 102 includes at least two notes (e.g., a top and a middle note, two middle notes, a top and a base note, etc.). In some embodiments, each fragrance exposed to the subject 102 includes at least three notes (e.g., a top, a middle, and a base note (vertical accord), three middle notes (a horizontal accord), etc.) In any case, the characteristic parameters (e.g., top notes, middle notes, and/or base notes) of the fragrances exposed to the subject 102 are known and stored in the product data store 318. In some embodiments, the characteristic parameters are stored, for example, as a note diagram.

In some embodiments, a user interface engine 308 of the mobile computing device 104 optionally presents a questionnaire to the subject 102 at bock 612. In some embodiments, the questionnaire may include questions that directly represent values for the subject 102. For example, the questionnaire may expressly ask the subject 102 to input a preference for fragrances, including specific product names, preferred notes, or other fragrance characteristics, such as whether the subject likes masculine, feminine or unisex fragrances, etc. In other embodiments, the user interface engine 308 presents one or more questions to the subject 102, the answers of which can be used to infer the subject preferences mentioned above or others. In some embodiments, the responses from the questionnaire can be used to verify the results generated by the facial analysis engine 312 and/or the recommendation engine 314.

At block 614, the user interface engine 308 receives responses to the questionnaire and transmits the responses to the questionnaire analysis engine 310 for processing. At block 616, the questionnaire analysis engine 310 determines one or more fragrance preferences based on the responses to the questionnaire. In some embodiments, the responses are processed by the questionnaire analysis engine 310 residing on the mobile computing device 104. In other embodiments, the responses are processed by the questionnaire analysis engine 310 residing on the server computing device 108. The user interface engine 308 may receive the responses via input into the user interface presented on the display device 302. The responses from the questionnaire and the results from processing the responses may be stored in the user data store 316. It will be appreciated that the actions performed at blocks 612 and 614 are also optional.

At block 618, a recommendation engine 314 determines a product recommendation based on at least the GSR data, and optionally, the preferences of the subject determined by the questionnaire engine 310 and/or the facial image analysis engine 312. In doing so, the recommendation engine 314 may access data from the product data store 316. In some embodiments, the product recommendation is a particular product. In other embodiments, the product recommendation is a fragrance profile. In some embodiments, the product recommendation is determined by the recommendation engine 314 residing on the mobile computing device 104. In other embodiments, the product recommendation is determined by recommendation engine 314 residing on the server computing device 108.

At block 620, the product recommendation is presented to the subject. For example, in one embodiment in which a specific product is presented, the product recommendation can be displayed on the display device 302 along with, for example, a description (e.g., note profile) of the product, the price of the product, where the product can be purchased, etc. In other embodiments in which the product recommendation is in the form of a fragrance profile, the fragrance profile may be displayed to a fragrance consultant by the display device 302. With the assistance of the fragrance consultant, one or more products may be presented to the subject based on the fragrance profile.

The method 600 then proceeds to an end block and terminates.

Figure 7:
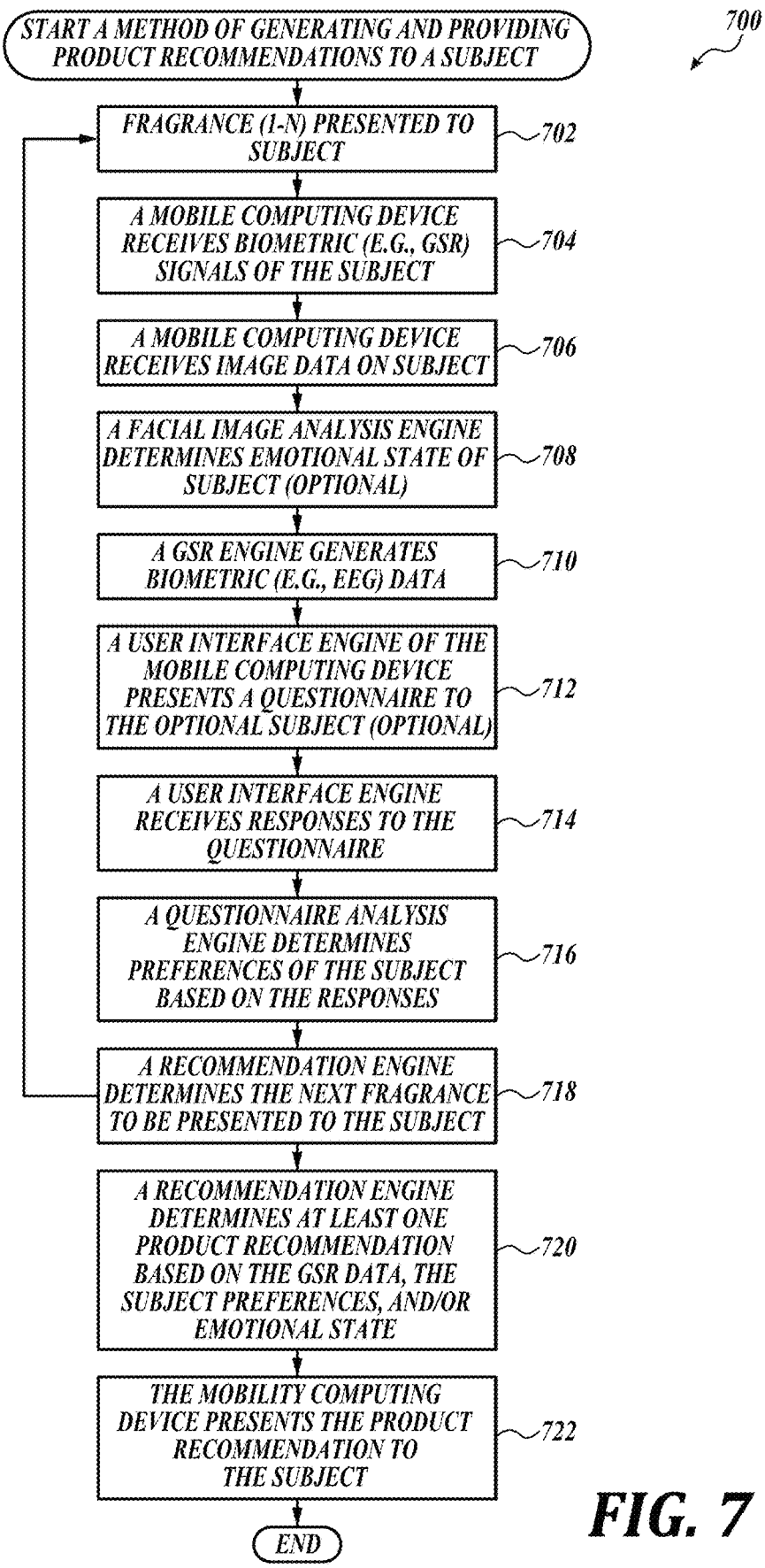
FIG. 7 is a flowchart that illustrates another non-limiting example of a method of generating and providing product recommendations to a subject according to an aspect of the present disclosure.

FIG. 7 is a flowchart that illustrates another non-limiting example of a method for generating and/or providing product recommendations to a subject according to one or more aspects of the present disclosure. The representative method, generally designated 700, will be described with references to one or more components of the system 100 depicted in FIGS. 1-5. The method 700 is substantially similar to the method 600 described above with reference to FIG. 6 except for the differences that will now be described.

In the embodiment of FIG. 7, the actions of blocks 702-716 are performed for each fragrance exposed to the subject. In this embodiment, instead of the fragrances being preselected, the recommendation engine 314, or other engine(s) of the system 100, determines at block 718 the next fragrance to be presented to the subject 102 based on the biometric data generated from exposure to the preceding fragrance. In some embodiments, the recommendation engine 314 determines the next fragrance to be presented to the subject 102 based on the biometric data generated from exposure to the preceding fragrance and the emotional state of the subject from block 708. In some other embodiments, the recommendation engine 314 determines the next fragrance to be presented to the subject 102 based on the biometric data generated from exposure to the preceding fragrance, the emotional state of the subject from block 708, and one or more responses from the questionnaire from block 716. Once all of the fragrances have been presented to the subject 102, the method 700 then proceeds to block 720, where the recommendation engine 314 determines a product recommendation. Of course, in some embodiments, blocks 706, 708, 712, and 714, and 716 are optional.

In some embodiments, the first fragrance to be selected is determined based on one or more responses from the questionnaire. Accordingly, the questionnaire can be presented to the subject prior to any exposure to a fragrance.

The detailed description set forth above in connection with the appended drawings, where like numerals reference like elements, are intended as a description of various embodiments of the present disclosure and are not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result. Moreover, some of the method steps can be carried serially or in parallel, or in any order unless specifically expressed or understood in the context of other method steps.

In the foregoing description, specific details are set forth to provide a thorough understanding of exemplary embodiments of the present disclosure. It will be apparent to one skilled in the art, however, that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

The present application may also reference quantities and numbers. Unless specifically stated, such quantities and numbers are not to be considered restrictive, but exemplary of the possible quantities or numbers associated with the present application. Also in this regard, the present application may use the term "plurality" to reference a quantity or number. In this regard, the term "plurality" is meant to be any number that is more than one, for example, two, three, four, five, etc. The term "about," "approximately," etc., means plus or minus 5% of the stated value.

Throughout this specification, terms of art may be used. These terms are to take on their ordinary meaning in the art from which they come, unless specifically defined herein or the context of their use would clearly suggest otherwise.

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

The embodiments of the invention in which an exclusive property or privilege is claimed are defined as follows:

1. A fragrance recommendation system, comprising:

a plurality of sensors configured to sense an electrodermal response of a subject based on a response to an olfactory stimulus, wherein the olfactory stimulus is a fragrance comprising two or more notes consisting essentially of top notes, middle notes, and base notes, and wherein the electrodermal response consists of a Galvanic Skin Response (GSR) signal;

a user interface; and processing circuitry connected in communication with the plurality of sensors and to the user interface, the processing circuitry configured to:

receive a first GSR signal of the subject based on a first presented fragrance consisting of at least two fragrance notes;

process the first GSR signal to generate a first GSR data;

generate, based on the first GSR data, a recommended second presented fragrance consisting of at least two fragrance notes;

receive a second GSR signal of the subject based on the recommended second presented fragrance;

process the second GSR signal to generate a second GSR data;

generate, based on the first GSR data and the second GSR data, one or more instances of predicted base notes, top notes, or middle notes in the first and second presented fragrances;

generate, based on the first GSR data and the second GSR data, one or more instances of a predicted degree of desirability score in the first and second presented fragrances;

generate a product recommendation based on the generated instances of predicted base notes, top notes, or middle notes, and the predicted degree of desirability score; and provide the product recommendation to the subject via the user interface, the product recommendation including one or more of a specific brand name of a fragrance or a visual representation of a fragrance profile.

2. The system of claim 1, wherein the processing circuitry is housed in a mobile computing device.

3. The system of claim 1, wherein the generated GSR data is represented as an image.

4. The system of claim 1, wherein the processing circuitry is configured to determine a product recommendation by comparing the data indictive of the generated instances to product data accessible by the one or more engines.

5. The system of claim 1, wherein the fragrance profile is presented to the subject as the product recommendation.

6. The system of claim 1, wherein the product recommendation is generated by comparing the fragrance profile with a set of fragrance profiles representing, respectively, a set of fragrances, the set of fragrance profiles accessible by the one or more engines.

7. The system of claim 1, further comprising a camera configured to capture data indicative of the emotional state of the subject based on the response to the olfactory stimulus, wherein the product recommendation is generated based at least on said GSR data and said data indicative of the emotional state of the subject.

8. The system of claim 1, wherein the processing circuitry is configured to detect the electrodermal response based on the response to an olfactory stimulus includes processing circuitry configured to:

detect a real-time cognitive process associated with an olfactory stimulus;

detect a variation in an electrical characteristics of the skin associated with a response to one or more fragrance accords;

detect a skin conductance based on a response to an olfactory stimulus;

detect a change in a skin potential associated with a response to an olfactory stimulus; or detect conductivity fluctuations indicative of a response to an olfactory stimulus.

9. A method for recommending a fragrance to a subject, comprising:

exposing the subject to a first presented fragrance consisting essentially of base notes, middle notes, and top notes, the subject having one or more Galvanic Skin Response (GSR) sensors coupled thereto;

obtaining a first GSR data of a subject from the one or more GSR sensors based on exposure to the first presented fragrance;

analyzing the first GSR data;

based on the first GSR data, generating by processor circuitry a recommended second presented fragrance consisting essentially of base notes, middle notes, and top notes;

exposing the subject to the second presented fragrance;

obtaining a second GSR data of the subject from the one or more GSR sensors based on exposure to the second presented fragrance;

analyzing the second GSR data;

based on at least the first GSR data and the second GSR data, generating by the processor circuitry one or more instances of predicted base notes, top notes, or middle notes in the fragrances and one or more instances of a predicted degree of desirability score;

generating, by the processor circuitry or other processor circuitry, a fragrance recommendation based on at least the generated instances of predicted base notes, top notes, or middle notes, and the predicted degree of desirability score; and presenting the fragrance recommendation to the subject.

10. The method of claim 9, wherein presenting the fragrance recommendation to the subject includes presenting a fragrance name to the subject based on a fragrance profile that comprises two or more notes that are preferred by the user; or presenting the fragrance profile to the subject.

11. The method of claim 9, further comprising obtaining questionnaire data of the subject indicative of a preference of a characteristic parameter of a product, wherein said fragrance recommendation is based on the analyzed biometric data and the questionnaire data.

12. The method of claim 10, wherein the fragrance recommendation is a name of a perfume.

13. The method of claim 10, wherein said generating a fragrance recommendation includes generating a fragrance profile of notes preferred by the user based on the GSR data, comparing the fragrance profile with a set of fragrance profiles representing, respectively, a set of fragrances to select a fragrance from the set of fragrances having a fragrance profile most similar to the generated fragrance profile.

14. The method of claim 9, further comprising obtaining data indicative of the emotional state of the subject based on the exposure to the fragrance, wherein said fragrance recommendation is based on the analyzed GSR data and said data indicative of the emotional state of the subject.

15. The method of claim 9, wherein presenting the fragrance recommendation to the subject includes displaying, by a display of a computing device, the fragrance recommendation to the subject.

\* \* \* \* \*